US011471120B2

(12) United States Patent
Xie

(10) Patent No.: US 11,471,120 B2
(45) Date of Patent: Oct. 18, 2022

(54) METHOD AND DEVICE FOR PROCESSING RAY DATA, STORAGE MEDIUM AND ELECTRONIC DEVICE

(71) Applicant: Neusoft Medical Systems Co., Ltd., Shenyang (CN)

(72) Inventor: Jiaxiang Xie, Shenyang (CN)

(73) Assignee: Neusoft Medical Systems Co., Ltd., Liaoning (CN)

( * ) Notice: Subject to any disclaimer, the term of this patent is extended or adjusted under 35 U.S.C. 154(b) by 65 days.

(21) Appl. No.: 17/236,977

(22) Filed: Apr. 21, 2021

(65) Prior Publication Data

US 2021/0393228 A1     Dec. 23, 2021

(30) Foreign Application Priority Data

Jun. 19, 2020   (CN) .......................... 202010568969.4

(51) Int. Cl.
*A61B 6/00* (2006.01)
*G01N 23/046* (2018.01)
*G06T 11/00* (2006.01)

(52) U.S. Cl.
CPC .......... *A61B 6/5205* (2013.01); *G01N 23/046* (2013.01); *G06T 11/006* (2013.01); *G06T 2207/10081* (2013.01)

(58) Field of Classification Search
CPC ..... A61B 6/5205; A61B 6/032; A61B 6/5258; A61B 6/06; A61B 6/035; G01N 23/046; G06T 11/006; G06T 2207/10081; G06T 11/005
See application file for complete search history.

(56) References Cited

U.S. PATENT DOCUMENTS

2018/0122107 A1* 5/2018 Li .......................... A61B 6/54

* cited by examiner

*Primary Examiner* — Courtney D Thomas
(74) *Attorney, Agent, or Firm* — Fish & Richardson P.C.

(57) ABSTRACT

Methods, devices, and systems for processing ray data are provided. The methods include: smoothing initial ray data based on collection of a detector of a CT device through at least two time windows to obtain smoothed ray data corresponding to each time window having a different window length, the initial ray data including attenuation values of rays passing through an object to be examined and being obtained at a sampling frequency within a specified time period, determining initial fluctuating data based on the initial ray data and smoothed ray data corresponding to one of the time windows, the initial fluctuating data being associated with a fluctuation due to occlusion of the rays by a collimator of the CT device, and removing the fluctuation from the initial ray data to obtain target ray data based on the smoothed ray data corresponding to each time window and the initial fluctuating data.

20 Claims, 7 Drawing Sheets

METHOD AND DEVICE FOR PROCESSING RAY DATA, STORAGE MEDIUM AND ELECTRONIC DEVICE

CROSS REFERENCE TO RELATED APPLICATIONS

This application claims priority to Chinese Patent Application No. 202010568969.4, entitled "METHOD AND DEVICE FOR PROCESSING RAY DATA, STORAGE MEDIUM AND ELECTRONIC DEVICE," filed on Jun. 19, 2020, the entire content of which is incorporated herein by reference.

TECHNICAL FIELD

The present disclosure relates to the field of electronic information technology, and in particular to methods, devices, and systems for processing ray data.

BACKGROUND

With the continuous development of the image processing technology, Computed Tomography (CT) devices have been widely used in the medical field. The CT devices use precisely collimated rays (such as X-rays, y-rays, ultrasound, etc.), together with a highly sensitive detector, to rotate about and scan a certain part of the human body, so as to obtain a CT image of that part. The CT devices have characteristics of short scanning time and clear images, which may assist doctors in observing the condition of the part.

SUMMARY

In general, one innovative aspect of the subject matter described in this present disclosure can be embodied in methods that include the actions of processing ray data for a Computed Tomography (CT) device, including: smoothing initial ray data based on collection of a detector of the CT device through at least two time windows to obtain smoothed ray data corresponding to each of the at least two time windows, where a window length of each of the at least two time windows is different, the initial ray data includes attenuation values of rays passing through an object to be examined, and the initial ray data is obtained at a sampling frequency within a specified time period; determining initial fluctuating data in the initial ray data based on the initial ray data and smoothed ray data corresponding to one of the at least two time windows, where the initial fluctuating data is associated with a fluctuation of the initial ray data due to occlusion of the rays by a collimator of the CT device that is configured to direct the rays towards the object to be examined; and removing the fluctuation from the initial ray data to obtain target ray data based on the smoothed ray data corresponding to each of the at least two time windows and the initial fluctuating data.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination.

In some embodiments, removing the fluctuation from the initial ray data to obtain the target ray data includes: determining one or more boundary intervals based on the smoothed ray data corresponding to each of the at least two time windows; dividing the initial fluctuating data into first fluctuating data and second fluctuating data based on the one or more boundary intervals, where a peak-to-peak value of the first fluctuating data is less than a peak-to-peak value of the second fluctuating data; replacing the second fluctuating data in the initial fluctuating data based on the first fluctuating data to obtain target fluctuating data; and obtaining the target ray data based on a difference between the initial ray data and the target fluctuating data.

In some embodiments, determining the one or more boundary intervals based on the smoothed ray data corresponding to each of the at least two time windows includes: determining the one or more boundary intervals based on differences of the smoothed ray data corresponding to each pair of two time windows of the at least two time windows, where the one or more boundary intervals include one or more first fluctuating intervals and one or more second fluctuating intervals; and obtaining the first fluctuating data based on data in the one or more first fluctuating intervals of the initial fluctuating data and the second fluctuating data based on data in the one or more second fluctuating intervals of the initial fluctuating data.

In some embodiments, replacing the second fluctuating data in the initial fluctuating data based on the first fluctuating data to obtain the target fluctuating data includes: converting the first fluctuating data into a fluctuating spectrum; determining a fluctuating period corresponding to the fluctuation due to the occlusion of the rays by the collimator based on the fluctuating spectrum; obtaining replacement data, whose duration is the fluctuating period, from the first fluctuating data; and replacing the second fluctuating data in the initial fluctuating data with the replacement data to obtain the target fluctuating data.

In some embodiments, determining the fluctuating period corresponding to the fluctuation due to the occlusion of the rays by the collimator includes: determining a frequency point of a peak in the fluctuating spectrum; and determining the fluctuating period based on the frequency point of the peak, the sampling frequency, and the specified time period.

In some embodiments, determining the initial fluctuating data in the initial ray data based on the initial ray data and the smoothed ray data corresponding to the one of the at least two time windows includes: determining the initial fluctuating data based on a difference between the initial ray data and the smoothed ray data corresponding to the one of the at least two time windows.

In some embodiments, determining the initial fluctuating data in the initial ray data based on the initial ray data and the smoothed ray data corresponding to the one of the at least two time windows includes: obtaining the initial fluctuating data by filtering the difference with an attenuation threshold to remove data that exceeds the attenuation threshold in the difference.

In some embodiments, the actions further includes: generating a CT image of the object based on the target ray data.

In some embodiments, the rays are emitted from a ray emitter of the CT device, the collection includes second rays collected by the detector, the second rays being formed by the rays passing through the object to be examined, and the attenuation values include differences between a first number of photons of the rays and a second number of photons of the second rays.

Another aspect of the present disclosure features an electronic device including: a ray emitter configured to emit first rays; a collimator configured to direct the first rays toward an object to be examined; and a detector configured to collect second rays that are formed by the first rays passing through the object to be examined; at least one processor; and at least one memory coupled to the at least one processor and storing programming instructions for execution by the at least one processor to perform the actions as described above.

The exemplary embodiments will be described in detail here, and examples thereof are illustrated in the accompanying drawings. When the following description refers to the accompanying drawings, unless otherwise stated, the same reference signs in different drawings designate the same or similar elements. The implementation manners described in the following exemplary embodiments do not represent all implementation manners consistent with the present application. On the contrary, they are merely examples of devices and methods consistent with some aspects of the present application as defined in the appended claims.

DETAILED DESCRIPTION

Figure 1A:
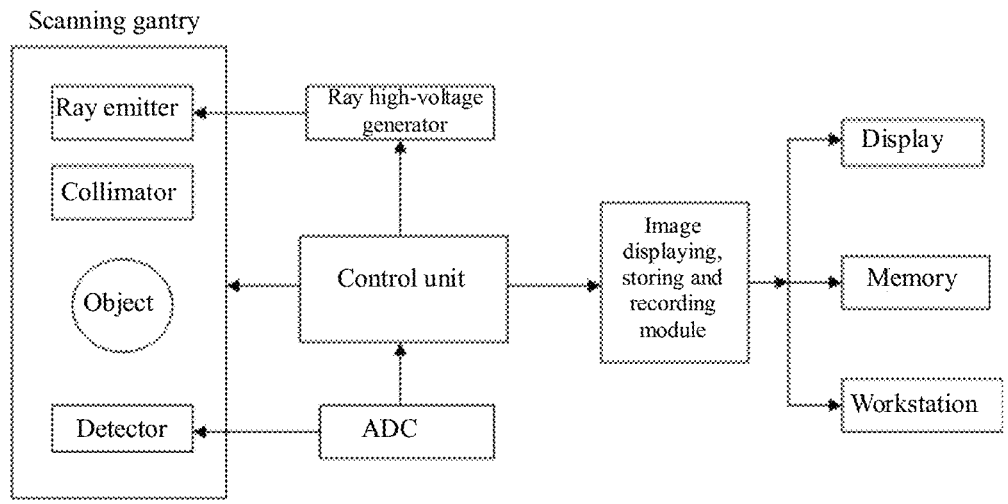
FIG. 1A is a schematic diagram showing a CT device according to one or more embodiments of the present disclosure.

FIG. 1A shows a CT device that includes a ray emitter, a collimator, and a detector, and the ray emitter, the collimator, and the detector together form a scanning gantry. The ray emitter can be configured to emit first rays to pass through the collimator and to be directed toward an object to be examined, and the detector can be configured to collect second rays formed from the first rays penetrating the object to be examined. It is noted that the rays mentioned in the examples of the present disclosure may be X-rays, y-rays, ultrasonic waves, etc., which are not specifically limited in the present disclosure. The CT device may also include a ray high-voltage generator, an Analog/Digital Converter (ADC), and a control unit. The ray high-voltage generator is configured to cause the ray generator to emit the first rays, and the ADC is configured to convert an analog signal collected by the detector into a digital signal (e.g., initial ray data described below), and send the digital signal to the control unit. The control unit is configured to process the digital signal and generate a CT image based on the digital signal. Further, the CT device may include an image displaying, storing and recording module (for example, display, memory, workstation, etc.). The entity for performing the method of processing ray data provided in the present disclosure may be understood as the aforementioned control unit. The control unit may be, for example, a Microcontroller Unit (MCU), an Electronic Control Unit (ECU), a terminal device (for example, laptop, tablet or desktop computer), or a server. In some examples, the control unit can be a processor.

Figure 1B:
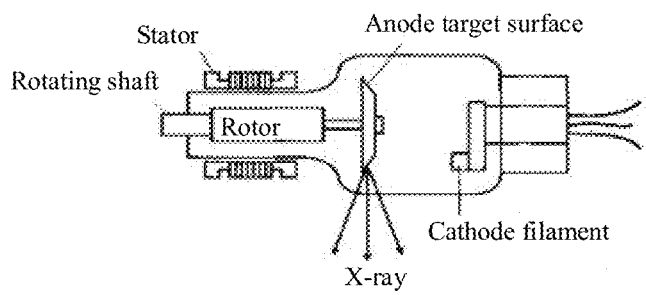
FIG. 1B is a schematic diagram showing an X-ray bulb tube in a CT device according to one or more embodiments of the present disclosure.
Figure 1C:
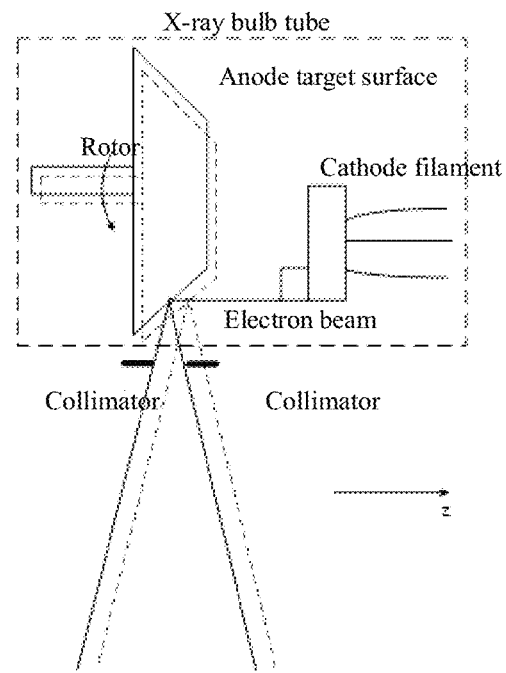
FIG. 1C is a schematic diagram showing the relative position of an X-ray bulb tube and a collimator in a CT device according to one or more embodiments of the present disclosure.

When the ray generator is a rotating anode X-ray bulb tube, as shown in FIG. 1B, an anode end can be composed of an anode target surface, a stator, a rotor, a rotating shaft, and a bearing (not shown). The anode target surface is in a shape of a disk. A center of the disk is fixed at an end of the rotating shaft at a center of the rotor. A magnetic field generated by the stator coil causes the rotor to rotate, which in turn drives the anode target surface to rotate at a high speed. In this way, an electron beam emitted via the cathode filament hits the anode target surface to generate heat, and the heat is distributed in an annular area of the continuously moving anode target surface, thereby reducing a temperature of the anode target surface. However, during the high-speed rotation of the rotor, due to the effect of the bearing clearance and gravity, a periodic position deflection of the rotor occurs, so that the anode target surface on the rotating shaft can also be deflected, causing the X-rays to deviate from the desired position. A relative position of the collimator and the rotating anode X-ray bulb tube in the CT device is fixed, as shown in FIG. 1C, so X-rays can be periodically occluded by the collimator. That is, the X-rays in the direction in which the electron beam is emitted, e.g., the z-axis direction, can be periodically occluded by the collimator, thereby resulting in fluctuating data in the X-ray data collected by the detector.

Implementations of the present disclosure provide methods, devices, storage media, and systems for processing ray data, e.g., applied in a CT device such as the CT device illustrated in FIGS. 1A-1C, which can remove the fluctuating data in the ray data. A detector of the CT device collects rays passing through an object to be examined, and initial ray data is obtained based on the collected rays. The initial ray data is further smoothed through multiple time windows to extract initial fluctuating data, which can reflect the fluctuation, from the initial ray data. Then fluctuation removal processing of the initial ray data is performed based on the initial fluctuating data and the smoothed data, so that the fluctuation caused by the rays periodically occluded by a collimator of the CT device is removed, which can improve the accuracy of the ray data.

Figure 2:
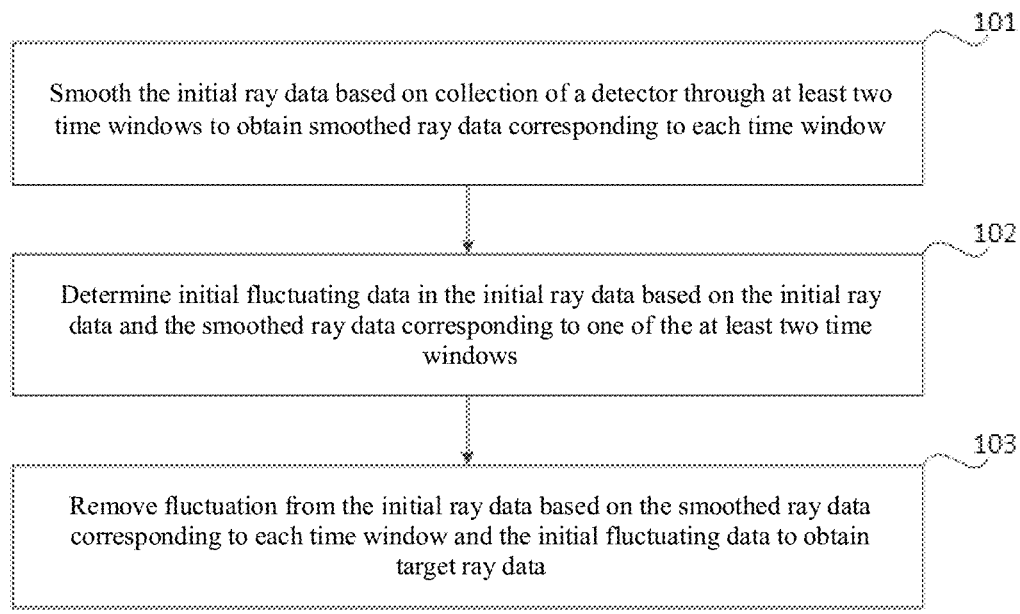
FIG. 2 is a flowchart showing a method of processing ray data according to one or more embodiments of the present disclosure.

FIG. 2 is a flow chart of a process showing a method of processing ray data according to one or more embodiments of the present disclosure. The method can be applied to a CT device, e.g., the CT device of FIGS. 1A-1C. The CT device includes a ray emitter (e.g., the ray emitter of FIG. 1A), a collimator (e.g., the collimator of FIGS. 1A, 1C), and a detector (e.g., the detector of FIG. 1A). The process can include steps 101 to 103 as described below.

At step 101, initial ray data based on collection of the detector is smoothed through at least two time windows to obtain smoothed ray data corresponding to each time window. A window length of each time window is different. The initial ray data includes attenuation values of first rays passing through the object to be examined, and the initial ray data is obtained at a sampling frequency within a specified time period.

Figure 3:
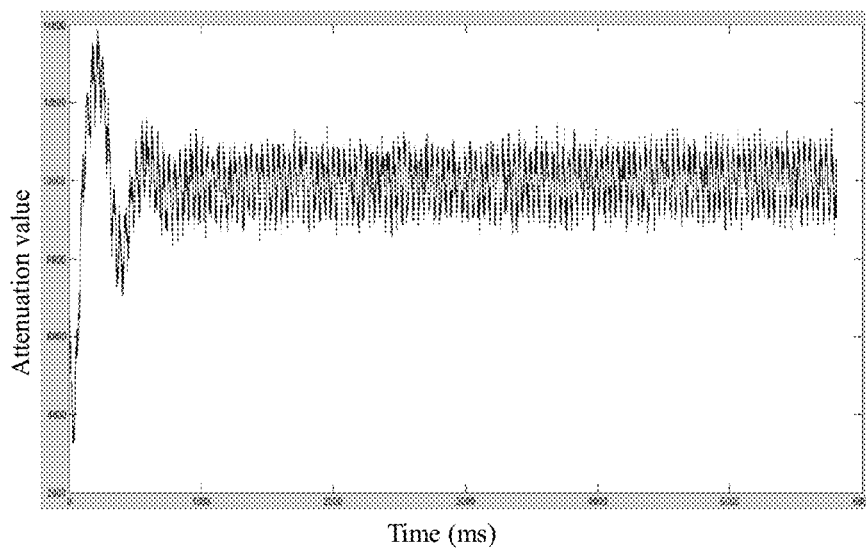
FIG. 3 shows initial ray data according to one or more embodiments of the present disclosure.

In some examples, the ray emitter emits the first rays, and the first rays pass through the collimator and are directed toward an object to be examined (for example, a particular part of human body), and the detector collects second rays formed from the first rays penetrating the object to be examined. The object to be examined absorbs a part of the first rays, so the second rays collected by the detector are different from the first rays emitted by the ray emitter. Densities of different parts of the object to be examined can be determined based on the attenuation values of the first rays passing through the object to be examined, and the determined densities of the different parts of the object can be used to generate a CT image of the object. The attenuation values can be determined based on the second rays and the first rays. For example, the detector can collect photons of the second rays, e.g., the first rays passing through the object to be examined, within a specified time period at a specified sampling frequency, and the CT device can obtain the attenuation values of the rays based on a number of the collected photons and a number of original photons of the first rays. The attenuation values can be considered as the initial ray data. Taking the sampling frequency of 1000 Hz (corresponding to a sampling period of 1 ms) and the specified time period of 6 s as an example, the initial ray data includes the attenuation values of the first rays passing through the object to be examined every 1 ms in 6 s (that is, the initial ray data includes data obtained at 6000 sampling time points). As shown in FIG. 3, the horizontal axis represents time, and the unit is ms, and the vertical axis represents the attenuation values of the first rays being emitted and passing through the object to be examined. The attenuation values can be the number of photons absorbed by the object to be examined, which can be obtained based on a difference between the number of photons received by the detector and the number of photons emitted by the ray emitter.

At least two time windows can be set in advance, and a window length (also referred to as a window width) of each time window can be different. Each time window can be configured for smoothing the initial ray data to obtain the smoothed ray data corresponding to each time window. The smoothed ray data corresponding to each time window can reflect the real data (e.g., the data with the fluctuation removed) included in the initial ray data in the time scale (e.g., the length of the time window) corresponding to the time window. For example, a corresponding window length of a first time window can be set to 50 ms, and a corresponding window length of a second time window can be set to 100 ms. Then, the first time window is configured for smoothing the initial ray data to obtain the first smoothed ray data, and the second time window is configured for smoothing the initial ray data to obtain the second smoothed ray data.

At step 102, initial fluctuating data included in the initial ray data is determined based on the initial ray data and the smoothed ray data corresponding to any one of the at least two time windows, where the initial fluctuating data can reflect fluctuation caused by occlusion of the first rays by the collimator.

Figure 4:
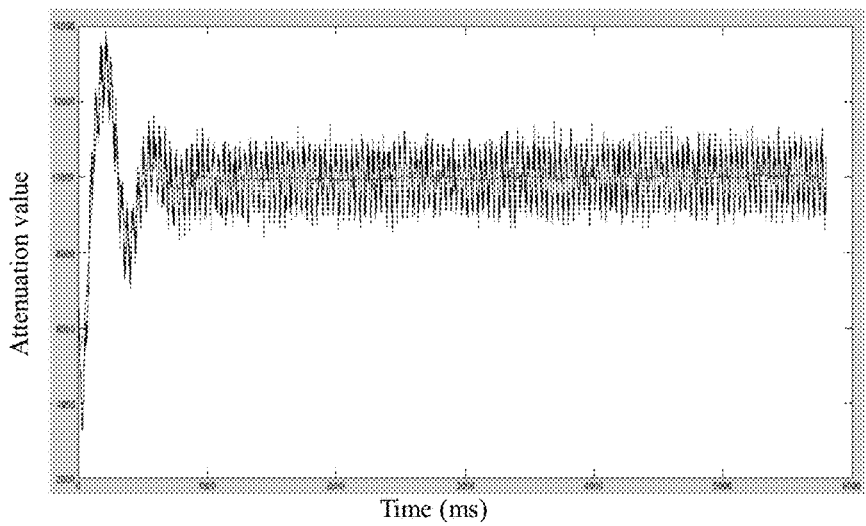
FIG. 4 shows initial ray data and smoothed ray data according to one or more embodiments of the present disclosure.
Figure 5:
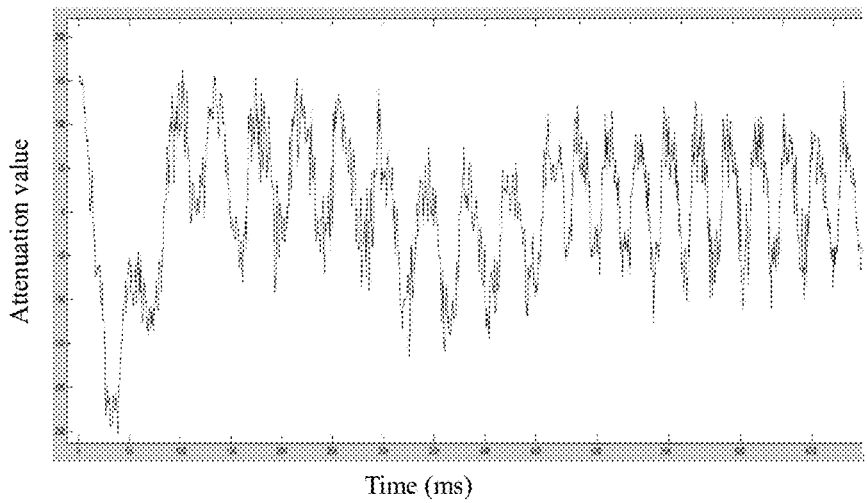
FIG. 5 shows initial fluctuating data according to one or more embodiments of the present disclosure.

In some examples, any time window can be selected from a plurality of time windows, and then the initial fluctuating data, which corresponds to fluctuations generated by the first rays being occluded by the collimator, is taken from the initial ray data, based on the smoothed ray data corresponding to the selected time window. In one implementation, the difference between the initial ray data and the smoothed ray data corresponding to any time window can be used as the initial fluctuating data. It is understood that the smoothed ray data corresponding to any time window can reflect the real data included in the initial ray data in the time scale corresponding to the time window, and the initial fluctuating data may be obtained by subtracting the smoothed ray data from the initial ray data. As shown in FIG. 4, the same curve lines in FIG. 4 and FIG. 3 are the initial ray data, and a curve with an overall trend same as that of the initial ray data but being more smooth is the first smoothed ray data corresponding to the first time window. The initial fluctuating data is shown in FIG. 5. In another implementation, the differences between the initial ray data and the smoothed ray data corresponding to any time window can be calculated firstly, and then the differences can be filtered with a preset first attenuation threshold to remove data that exceeds the first attenuation threshold. Since the first rays are periodically occluded by the collimator, the fluctuating data included in the initial ray data is also periodic. Besides, the attenuation values of the first rays passing through the object to be examined are to be within a specified range, so the interference caused by other external noises can be eliminated with the first attenuation threshold, thereby improving the effectiveness of the initial fluctuating data.

At step 103, the fluctuation in the initial ray data is removed based on the smoothed ray data corresponding to each of the at least two time windows and the initial fluctuating data, to obtain target ray data.

In some examples, after determining the initial fluctuating data, the initial fluctuating data may be further processed based on the smoothed ray data corresponding to each time window, so as to more accurately reflect the fluctuations caused by occlusion of the first rays by the collimator. Since the first rays are periodically occluded by the collimator, the fluctuating data included in the initial ray data is also periodic. If there is a severely fluctuating part (e.g., a drastically fluctuating part) in the initial fluctuating data, the severely fluctuating part may be included in the attenuation values of the first rays passing through the object to be examined. For example, when the CT device is just started to scan the object to be examined, the first rays emitted by the ray emitter are not stable, and the attenuation values of the corresponding first rays passing through the object to be examined can also fluctuate, resulting in a severely fluctuating part in the initial fluctuating data.

After a certain period of time, the first rays become stable, and thus the attenuation values of the first rays can become stable with slight fluctuation. Therefore, the initial fluctuating data can be divided into severely fluctuating data (or drastically fluctuating data) and slightly fluctuating data, based on the smoothed ray data corresponding to each time window. As the fluctuating data included in the initial ray data is periodic, the severely fluctuating data can be replaced with the slightly fluctuating data to obtain the target fluctuating data with slight or little fluctuation. For example, based on a time length corresponding to severely fluctuating data, data of that time length can be taken from the slightly fluctuating data, to replace the severely fluctuating data to obtain target fluctuating data. Finally, the target fluctuating data can be removed from the initial ray data to complete the fluctuation removal processing, and the obtained data is the target ray data. Compared with the initial ray data, in the target ray data, the fluctuating data caused by occlusion of the first rays by the collimator is removed, which can accurately reflect the attenuation of the first rays passing through the object to be examined, and improve the accuracy of the ray data.

In summary, the detector in the present disclosure collects second rays that are first rays passing through the object to be examined, and then initial ray data is determined based on the collected second rays and the first rays, and the initial ray data includes the attenuation values of the first rays passing through the object to be examined. The initial ray data can be obtained at the sampling frequency within a specified time period. Then, the initial ray data can be smoothed through at least two time windows with different window lengths to obtain the smoothed ray data corresponding to each time window. The initial fluctuating data included in the initial ray data can be further determined based on the initial ray data and the smoothed ray data corresponding to any time window. The initial fluctuating data can reflect the fluctuation due to occlusion of the first rays by the collimator. Finally, based on the smoothed ray data corresponding to each time window and the initial fluctuating data, fluctuation removal processing of the initial ray data can obtain the target ray data. In the present disclosure, as the initial ray data is smoothed through multiple time windows to obtain smoothed ray data and further initial fluctuating data that can reflect the fluctuation, and the fluctuation removal processing on the initial ray data is performed to remove the fluctuation due to occlusion of the first rays by the collimator, the accuracy of the target ray data can be improved.

Figure 6:
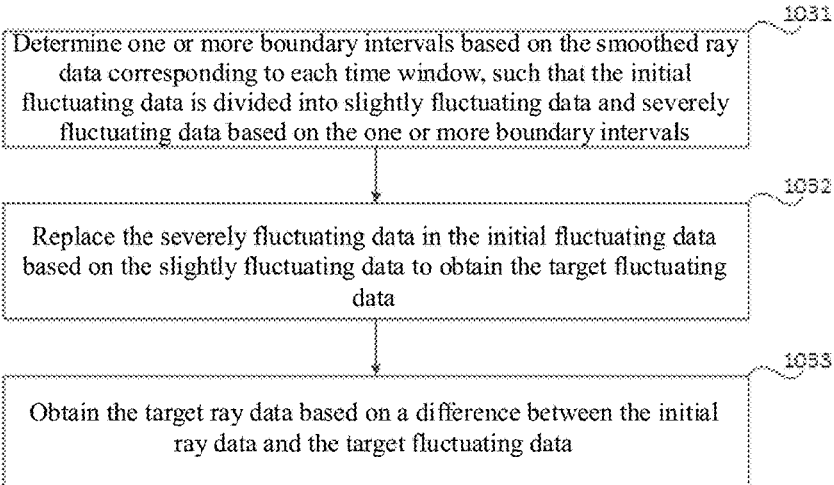
FIG. 6 is a flowchart showing another method of processing ray data according to one or more embodiments of the present disclosure.

FIG. 6 is a flowchart of a process showing another method of processing ray data according to one or more embodiments of the present disclosure. As shown in FIG. 6, the step 103 of FIG. 2 may include the following steps 1031 to 1033.

At step 1031, one or more boundary intervals are determined based on the smoothed ray data corresponding to each of the at least two time windows, such that the initial fluctuating data is divided into slightly fluctuating data and severely fluctuating data (e.g., drastically fluctuating data) based on the one or more boundary intervals, where a peak-to-peak value of the slightly fluctuating data is smaller than a peak-to-peak value of the severely fluctuating data.

For example, the one or more boundary intervals or data ranges may be determined based on the differences between the smoothed ray data corresponding to each pair of two time windows in the at least two time windows. In some examples, the at least two time windows include three time windows A, B, C. The one or more boundary intervals or data ranges can be determined based on a difference between the smoothed ray data corresponding to a pair of A and B time windows, a difference between the smoothed ray data corresponding to a pair of B and C time windows, and a difference between the smoothed ray data corresponding to a pair of A and C time windows. The fluctuation in the attenuation values of the first rays passing through the object to be examined may include: fluctuation in the attenuation values of the first rays passing through the object to be examined when the CT device scans the object to be examined and the ray emitter just starts to emit the first rays, and/or fluctuation in the attenuation values of the first rays passing through the object to be examined because the first rays have passed through an object with irregular shape and uneven density (for example, an object such as jewelry, belts and the like worn by the human body with a large difference in density from human organs). The first rays are periodically occluded by the collimator, and the corresponding fluctuation is also periodic. Therefore, the initial fluctuating data includes two parts. One part includes both the fluctuating data due to occlusion of the first rays by the collimator, and the fluctuating data generated by the attenuation values of the first rays passing through the object to be examined, that is, severely fluctuating data. The other part only includes the fluctuating data generated due to occlusion of the first rays by the collimator (at this time, the attenuation value of the first rays passing through the object to be examined has stabilized), that is, the slightly fluctuating data. The peak-to-peak value of the severely fluctuating data is greater than the peak-to-peak value of the slightly fluctuating data.

The one or more boundary intervals or data ranges are configured to identify which data in the initial fluctuating data belong to severely fluctuating data and which data in the initial fluctuating data belong to slightly fluctuating data. Therefore, the one or more boundary intervals or data ranges may be divided into two types of time intervals: slightly fluctuating interval and severely fluctuating interval. There may be a plurality of slightly fluctuating intervals and a plurality of severely fluctuating intervals in the initial fluctuating data. The slightly fluctuating intervals and the severely fluctuating intervals are staggered. Each slightly fluctuating interval includes start time and end time of the interval. Similarly, each severely fluctuating interval also includes start time and end time of the severely fluctuating interval. Then, after determining the one or more boundary intervals or data ranges, the data obtained in the severely fluctuating interval(s) in the initial fluctuating data can be regarded as the severely fluctuating data, and the data obtained in the slightly fluctuating interval(s) in the initial fluctuating data can be regarded as the slightly fluctuating data.

For example, if three or more time windows are applied to smooth the initial ray data at step 101, then the three or more time windows can be grouped in pairs. Differences between the smoothed ray data corresponding to each pair of two time windows can be calculated. The differences are divided by the threshold method, and thus the one or more boundary intervals or data ranges corresponding to each pair of two time windows are obtained. After that, the one or more boundary intervals corresponding to each pair of two time windows are averaged to obtain the one or more boundary intervals for dividing the initial fluctuating data. For example, if there are a first time window, a second time window, and a third time window, the boundary interval corresponding to the first time window and the second time window, the boundary interval corresponding to the second time window and the third time window, and the boundary interval corresponding to the first time window and the third time window can be calculated, respectively. Then the average of the three boundary intervals is used as the boundary interval for dividing the initial fluctuating data. If two time windows are applied to smooth the initial ray data at step 101, then the differences between the smoothed ray data corresponding to the two time windows can be calculated, and the differences are divided by the threshold method to obtain one or more boundary intervals.

Figure 7:
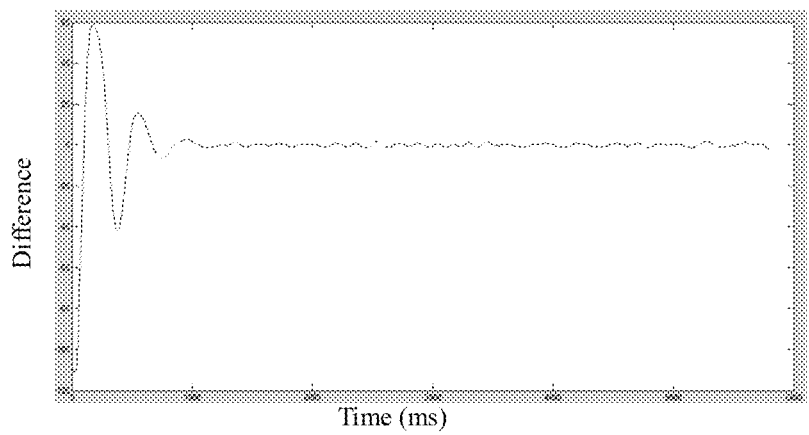
FIG. 7 shows differences between smoothed ray data corresponding to two time windows according to one or more embodiments of the present disclosure.

In an example, the differences between the smoothed ray data corresponding to two time windows are calculated, and the differences are divided by the threshold method to determine the boundary interval. Taking the window length of the first time window as 50 ms and the window length of the second time window as 100 ms as an example, the smoothed ray data corresponding to the second time window is subtracted from the smoothed ray data corresponding to the first time window to obtain the differences. The differences are shown in FIG. 7. It can be seen that the data can be shifted to near 0 by calculating the differences between the smoothed ray data corresponding to the first time window and the smoothed ray data corresponding to the second time window (for example, the differences between the smoothed ray data corresponding to the first time window and the smoothed ray data corresponding to the second time window is approximately 0), so that each of the differences can be compared with a preset second attenuation threshold (for example, 50). After comparing each of the differences with the second attenuation threshold, it can be determined that the absolute value of the differences between 80 ms and 6000 ms is less than the second attenuation threshold, and the absolute value of a plurality of differences in the differences between 0 and 80 ms are greater than or equal to the second attenuation threshold. Thus, the interval of 0 to 80 ms can be taken as a severely fluctuating interval, and the interval of 80 ms to 6000 ms can be taken as a slightly fluctuating interval. Taking the initial fluctuating data shown in FIG. 5 as an example, the data from 0 to 80 ms can be regarded as severely fluctuating data, and the data from 80 ms to 6000 ms can be regarded as slightly fluctuating data.

At step 1032, the severely fluctuating data in the initial fluctuating data is replaced with the slightly fluctuating data to obtain the target fluctuating data.

At step 1033, differences between the initial ray data and the target fluctuating data are taken as the target ray data.

For example, after dividing the initial fluctuating data into severely fluctuating data and slightly fluctuating data, the time length corresponding to the severely fluctuating data is firstly determined, and then a part of the slightly fluctuating data with the same time length as the severely fluctuating data is taken from the slightly fluctuating data, to replace the severely fluctuating data. The replaced severely fluctuating data (e.g., part of the slightly fluctuating data) and the slightly fluctuating data are combined in chronological order, to obtain the target fluctuating data. In this way, compared to the initial fluctuating data, the fluctuation caused by the attenuation value of the rays passing through the object to be examined due to the unstable rays is not included in the target fluctuating data, and the target fluctuating data can be more accurate to reflect the fluctuation due to periodic occlusion of the rays by the collimator. Finally, the target fluctuating data can be subtracted from the initial ray data to obtain the target ray data, which can accurately reflect the attenuation values of the first rays passing through the object to be examined, and improve the accuracy of the target ray data.

It is noted that in scenarios where there are multiple slightly fluctuating intervals and multiple severely fluctuating intervals, the initial fluctuating data can be divided into multiple groups of severely fluctuating data and multiple groups of slightly fluctuating data based on multiple slightly fluctuating intervals and multiple severely fluctuating intervals, and severely fluctuating data and slightly fluctuating data are arranged alternately. Then, when step 1032 is performed, in the process of replacing each group of severely fluctuating data, the replacement can be completed based on a group of slightly fluctuating data adjacent to a group of severely fluctuating data. It is also possible to complete the replacement, based on the slightly fluctuating data corresponding to the slightly fluctuating interval with the longest duration among the plurality of slightly fluctuating intervals, which is not specifically limited in the present disclosure.

In some implementations, step 1032 may include sub-steps 1032-1 to 1032-3.

At sub-step 1032-1, the slightly fluctuating data is converted into a slightly fluctuating spectrum.

Figure 8:
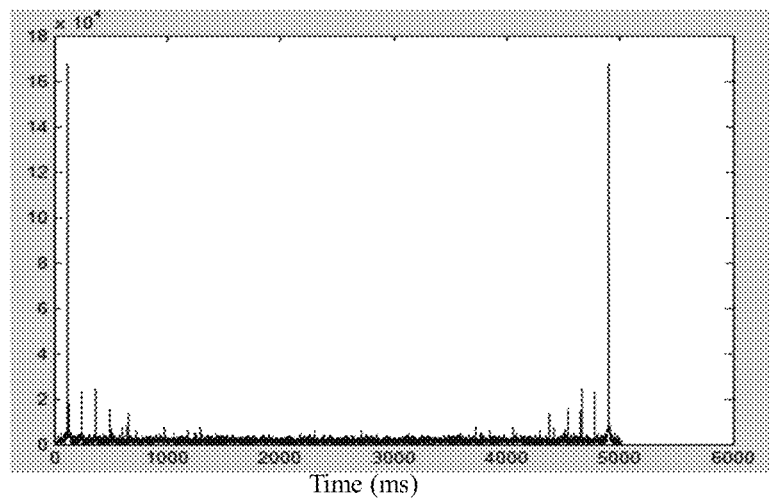
FIG. 8 shows a slightly fluctuating spectrum according to one or more embodiments of the present disclosure.

For example, taking the data obtained after 80 ms in the initial fluctuating data shown in FIG. 5 being slightly fluctuating data as an example, the slightly fluctuating data can be subject to Fourier transformation, to obtain the slightly fluctuating spectrum, as shown in FIG. 8.

At sub-step 1032-2, a fluctuating period corresponding to fluctuations due to occlusion of the first rays by the collimator is determined based on the slightly fluctuating spectrum.

The frequency point of the peak in the slightly fluctuating spectrum is found, and then the fluctuating period is determined based on the frequency point of the peak, the sampling frequency and the specified time period. For example, the sampling frequency SampleFreq=1/IntegrationTime, where IntegrationTime is the sampling period. The frequency point of the peak is MaxIndex, and the range of MaxIndex is 0 to N/2, where N is the number of samples (that is, the specified time period*SampleFreq). Then, the frequency of the position deflection of the rotor is WobblingFreq=SampleFreq*MaxIndex/N. Correspondingly, the corresponding fluctuating period of the fluctuation caused by the rays occluded by the collimator due to the position deflection of the rotor, Circle=SampleFreq/WobblingFreq=Specified time period*SampleFreq/MaxIndex.

At step 1032-3, replacement data whose duration is the fluctuating period is taken from the slightly fluctuating data, and the severely fluctuating data in the initial fluctuating data is replaced with the replacement data, to obtain the target fluctuating data.

Figure 9:
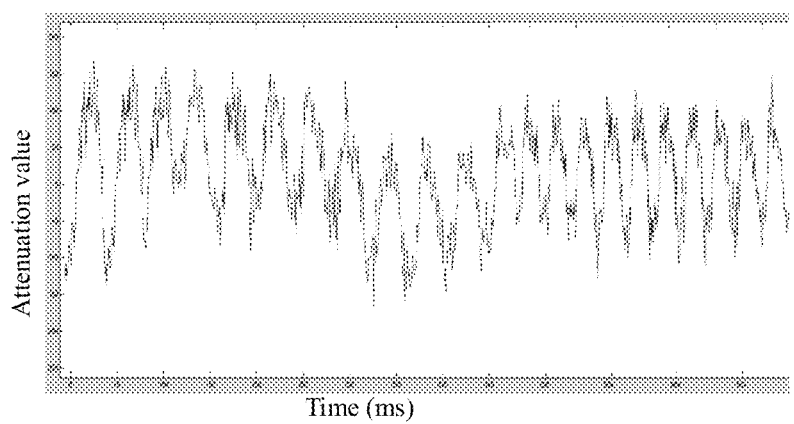
FIG. 9 is a target fluctuating spectrum according to one or more embodiments of the present disclosure.
Figure 10:
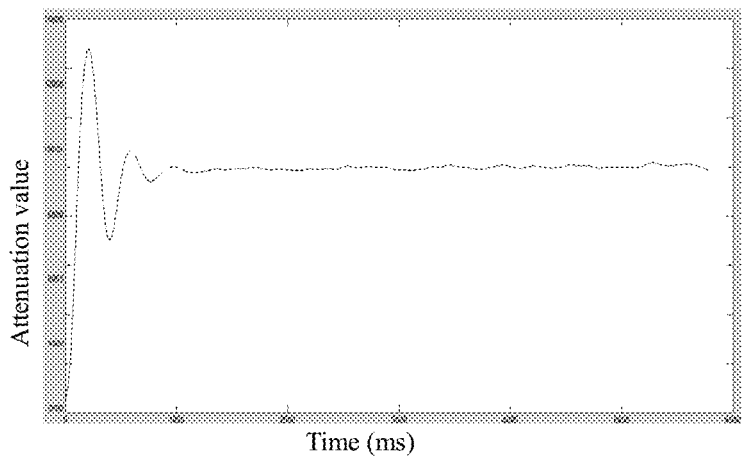
FIG. 10 shows a target ray spectrum according to one or more embodiments of the present disclosure.

Finally, to maintain the periodicity of the fluctuation, the replacement data whose duration is the fluctuating period can be taken from the slightly fluctuating data, and the severely fluctuating data in the initial fluctuating data can be replaced with the replacement data, based on the time length of the severely fluctuating data. For example, if the fluctuating period is 40 ms, and the time length of the severely fluctuating data is 80 ms, then the replacement data can be repeated twice (i.e., 80 ms/40 ms=2) to replace the severely fluctuating data. The replacement data repeated twice and the slightly fluctuating data are combined in chronological order, to obtain the target fluctuating data, as shown in FIG. 9. It can be seen that, compared with the initial fluctuating data shown in FIG. 5, the periodicity of the target fluctuating data in FIG. 9 is more apparent, and the fluctuation due to the rays being periodically occluded by the collimator is better reflected. Finally, the target fluctuating data can be subtracted from the initial ray data to obtain the target ray data, as shown in FIG. 10, which can accurately reflect the attenuation value of the first rays passing through the object to be examined, and improve the accuracy of the ray data.

Figure 11:
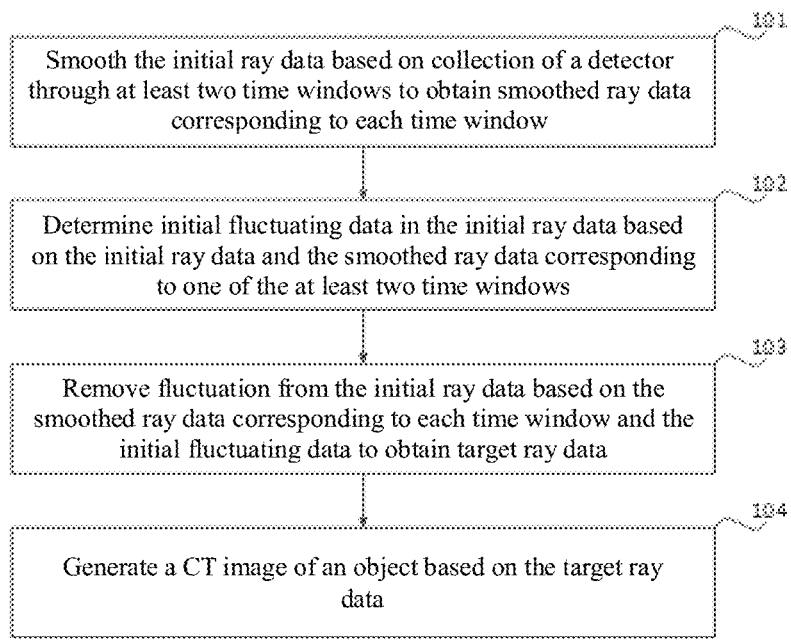
FIG. 11 is a flowchart showing another method of processing ray data according to one or more embodiments of the present disclosure.

FIG. 11 is a flowchart of a process showing another method of processing ray data according to an example. As shown in FIG. 11, after step 103, the process of the method further includes step 104. Steps 101 to 103 of FIG. 11 can be the steps 101 to 103 of FIG. 2.

At step 104, a CT image of the object to be examined is generated based on the target ray data.

Figures 12A, 12B:
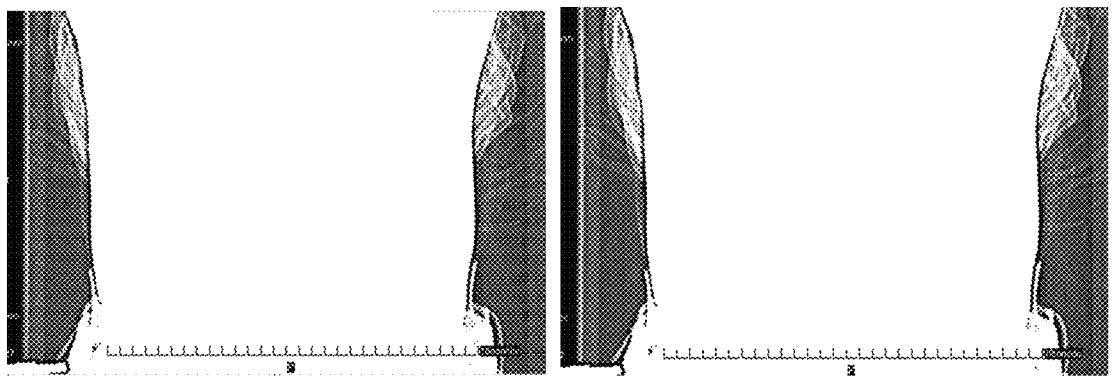
FIG. 12A is a CT image according to one or more embodiments of the present disclosure.
FIG. 12B is a CT image according to one or more embodiments of the present disclosure.

For example, after obtaining target ray data that can accurately reflect the attenuation values of the first rays passing through the object to be examined, a CT image of the object to be examined can be generated based on the target ray data. For example, the target ray data can be mapped into a CT image based on a preset mapping relationship between attenuation value of the first ray passing through the object to be examined and the brightness of the image. Since the fluctuating data caused by occlusion of the first rays by the collimator is removed from the target ray data, the horizontal streak artifacts in the CT image can be effectively removed. FIG. 12A shows a CT image generated directly from the initial ray data, and a large number of horizontal streak artifacts are seen from the image. FIG. 12B shows a CT image generated based on the target ray data. Compared with FIG. 12A, the horizontal streak artifact are effectively removed.

Figure 13:
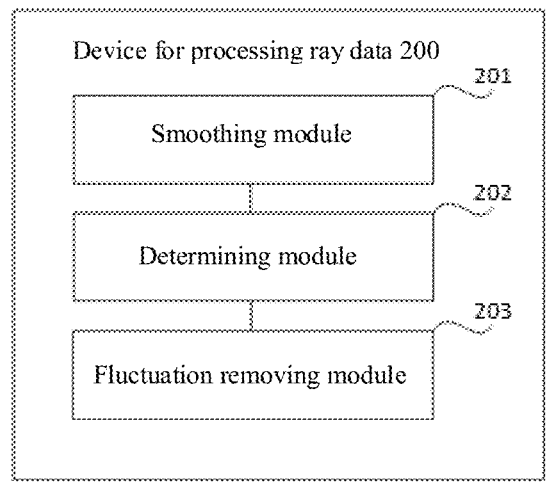
FIG. 13 is a block diagram showing a device for processing ray data according to one or more embodiments of the present disclosure.

FIG. 13 is a block diagram of a device for processing ray data according to one or more embodiments of the present disclosure. The device 200 is applied to a CT device. For example, the device 200 can be a control unit in the CT device, e.g., as illustrated in FIG. 1A, or a controller externally coupled to the CT device. The CT device includes a ray emitter, a collimator, and a detector. The emitter is configured to emit first rays that are directed toward the object to be examined through the collimator. The detector is configured to collect second rays that are formed from the first rays passing through the object to be examined. The device for processing the ray data can include a smoothing module 201, a determining module 202, and a fluctuation removing module 203.

The smoothing module 201 is configured to smooth the initial ray data obtained based on collection of the detector through at least two time windows, to obtain smoothed ray data corresponding to each time window. The window length of each time window is different. The initial ray data includes the attenuation value of the first rays passing through the object to be examined, and the initial ray data is obtained at the sampling frequency within a specified time period. In some examples, the smoothing module can be a smoothing circuit.

The determining module 202 is configured to determine the initial fluctuating data included in the initial ray data based on the initial ray data, and the smoothed ray data corresponding to any time window. The initial fluctuating data can reflect the fluctuation caused by the first rays being occluded by the collimator. In some examples, the determining module can be a determining circuit.

The fluctuation removing module 203 is configured to remove the fluctuation in the initial ray data, based on the smoothed ray data corresponding to each of the at least two time windows and the initial fluctuating data, to obtain target ray data. In some examples, the fluctuation removing module can be a fluctuation removing circuit.

Figure 14:
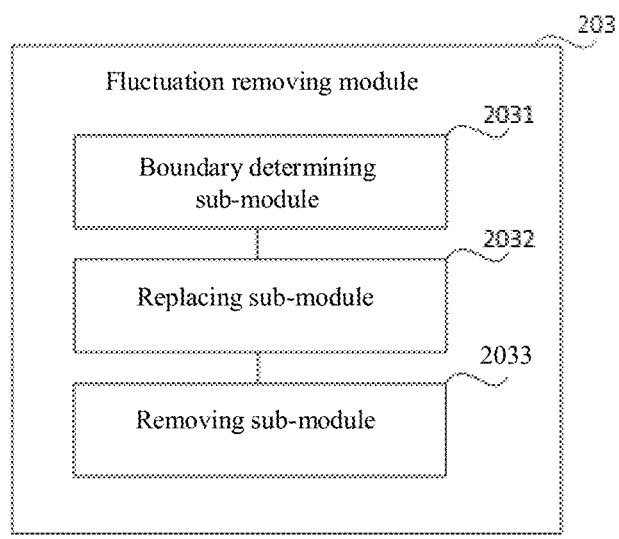
FIG. 14 is a block diagram showing another device for processing ray data according to one or more embodiments of the present disclosure.

FIG. 14 is a block diagram showing another device of processing ray data according to one or more embodiments of the present disclosure. As shown in FIG. 14, the fluctuation removing module 203 may include a boundary determining sub-module 2031, a replacing sub-module 2032, and a removing sub-module 2033.

A boundary determining sub-module 2031 is configured to determine one or more boundary intervals based on the smoothed ray data corresponding to each of the at least two time windows, such that the initial fluctuating data is divided into slightly fluctuating data and severely fluctuating data based on the one or more boundary intervals, where a peak-to-peak value of the slightly fluctuating data is less than a peak-to-peak value of the severely fluctuating data.

A replacing sub-module 2032 is configured to replace the severely fluctuating data in the initial fluctuating data with the slightly fluctuating data to obtain the target fluctuating data.

A removing sub-module 2033 is configured to use the differences between the initial ray data and the target fluctuating data as the target ray data.

The boundary determining sub-module 2031 is configured to execute the following steps 1) to 2).

In step 1), the one or more boundary intervals are determined based on the differences between the smoothed ray data corresponding to each pair of two time windows of the at least two time windows. The boundary interval includes one or more slightly fluctuating intervals and one or more severely fluctuating intervals.

In step 2), the data obtained in the one or more severely fluctuating intervals in the initial fluctuating data can be regarded as the severely fluctuating data, and the data obtained in the one or more slightly fluctuating intervals in the initial fluctuating data can be regarded as the slightly fluctuating interval.

The replacing sub-module 2032 is configured to perform the following steps 3) to 5).

In step 3), the slightly fluctuating data is converted into a slightly fluctuating spectrum.

In step 4), a fluctuating period corresponding to the fluctuation due to the first rays being occluded by the collimator is determined, based on the slightly fluctuating spectrum.

In step 5), the replacement data whose duration is the fluctuating period is taken from the slightly fluctuating interval, and the severely fluctuating data in the initial fluctuating data is replaced with the replacement data, to obtain the target fluctuating data.

In some embodiments, the replacing sub-module 2032 can be configured to perform the following operations.

First, a frequency point of a peak in the smooth fluctuating spectrum is determined.

After that, the fluctuating period is determined based on the frequency point of the peak, the sampling frequency and the specified duration.

The determining module 202 can be configured to perform the following operations.

The differences between the initial ray data and the smoothed ray data corresponding to any time window can be used as the initial fluctuating data.

Figure 15:
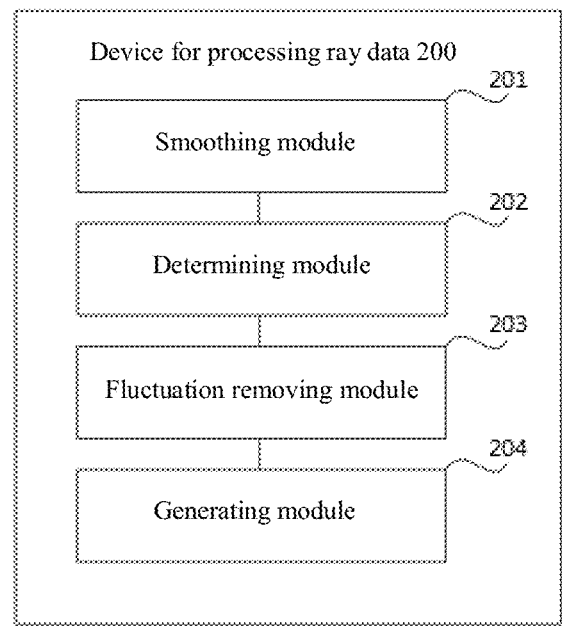
FIG. 15 is a block diagram showing another device for processing ray data according to one or more embodiments of the present disclosure.

FIG. 15 is a block diagram showing another device for processing ray data according to one or more examples. As shown in FIG. 15, the device 200 further includes a generating module 204.

The generating module 204 is configured to generate a CT image of the object to be examined based on the target ray data after the target ray data is obtained by performing fluctuation removal processing on the initial ray data based on the smoothed ray data corresponding to each time window and the initial fluctuation data.

Regarding the device in the foregoing examples, the specific manner in which each module performs operation has been described in detail in the one or more examples of the method, and detailed description will not be given here.

In summary, the detector in the present disclosure collects second rays that are first rays passing through the object to be examined, and then initial ray data is determined based on the collected second rays and the first rays, and the initial ray data includes the attenuation values of the first rays passing through the object to be examined. The initial ray data can be obtained at the sampling frequency within a specified time period. Then, the initial ray data can be smoothed through at least two time windows with different window lengths to obtain the smoothed ray data corresponding to each time window. The initial fluctuating data included in the initial ray data can be further determined based on the initial ray data and the smoothed ray data corresponding to any time window. The initial fluctuating data can reflect the fluctuation due to occlusion of the first rays by the collimator. Finally, based on the smoothed ray data corresponding to each time window and the initial fluctuating data, fluctuation removal processing of the initial ray data can obtain the target ray data. In the present disclosure, as the initial ray data is smoothed through multiple time windows to obtain smoothed ray data and further initial fluctuating data that can reflect the fluctuation, and the fluctuation removal processing on the initial ray data is performed to remove the fluctuation due to occlusion of the first rays by the collimator, the accuracy of the target ray data can be improved.

Figure 16:
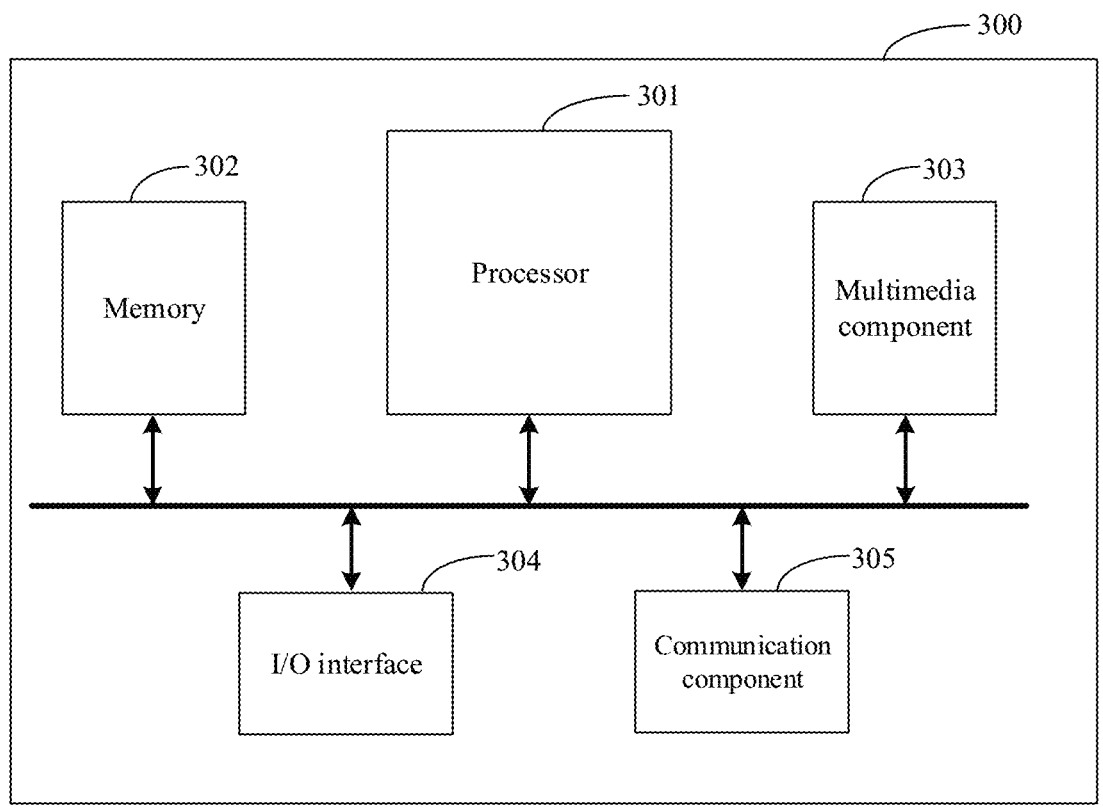
FIG. 16 is a block diagram showing an electronic device according to one or more embodiments of the present disclosure.

FIG. 16 is a block diagram showing an electronic device 300 according to one or more embodiments of the present disclosure. As shown in FIG. 16, the electronic device 300 may include a processor 301 and a memory 302. The electronic device 300 may further include one or more of a multimedia component 303, an input/output (I/O) interface 304, and a communication component 305.

The processor 301 is configured to control the overall operation of the electronic device 300 to complete all or part of the steps in the above-mentioned method of processing ray data. The memory 302 is configured to store various types of data to support operations on the electronic device 300. These data may include, for example, instructions for any application or method to operate on the electronic device 300, as well as application-related data, for example, contact data, messages sent and received, pictures, audio, video, etc. The memory 302 can be implemented by any type of volatile or non-volatile storage device or a combination thereof, such as static random access memory (referred briefly to as SRAM), electrically erasable programmable read-only memory (referred briefly to as EEPROM), Erasable Programmable Read-Only Memory (referred briefly to as EPROM), Programmable Read-Only Memory (referred briefly to as PROM), Read only Memory (referred briefly to as ROM), magnetic memory, flash memory, magnetic disk or optical disk. The multimedia component 303 may include a screen and an audio component. The screen may be a touch screen, for example, and the audio component is configured to output and/or input audio signals. For example, the audio component may include a microphone, which is configured to receive external audio signals. The received audio signals can be further stored in the memory 302 or sent through the communication component 305. The audio component also includes at least one speaker for outputting audio signals. The I/O interface 304 provides an interface between the processor 301 and other interface modules. The above-mentioned interface modules may be a keyboard, a mouse, a button, and the like. These buttons can be virtual buttons or physical buttons. The communication component 305 is configured for wired or wireless communication between the electronic device 300 and other devices. Wireless communication is, such as Wi-Fi, Bluetooth, Near Field Communication (referred briefly to as NFC), 2G, 3G, 4G, NB-IOT, eMTC, or 5G, etc., or one or a combination of them, which is not limited here. Therefore, the corresponding communication component 305 may include a Wi-Fi module, a Bluetooth module, an NFC module, and so on.

In an example, the electronic device 300 may be implemented by one or more application specific integrated circuits (referred briefly to as ASIC), digital signal processor (referred briefly to as DSP), Digital Signal Processing Device (referred briefly to as DSPD), Programmable Logic Device (referred briefly to as PLD), Field Programmable Gate Array (referred briefly to as FPGA), controller, microcontroller, microprocessor or other electronic components, which executes the above-mentioned method of processing ray data.

In another example, there is also provided a computer-readable storage medium including program instructions thereon. When program instructions are executed by a processor, the steps of the above-mentioned method of processing ray data are implemented. For example, the computer-readable storage medium may be the foregoing memory 302 including program instructions, which may be executed by the processor 301 of the electronic device 300 to complete the foregoing method of processing ray data.

The preferred examples of the present disclosure are described in detail above with reference to the accompanying drawings. However, the present disclosure is not limited to the specific details in the above-mentioned examples. Within the scope of the technical concept of the present disclosure, various simple modifications can be made to the technical solutions of the present disclosure. These simple modifications all belong to the protection scope of the present disclosure.

In addition, it is noted that the various specific technical features described in the above-mentioned specific examples can be combined in any suitable manner without contradiction. To avoid unnecessary repetition, various possible combinations are not described separately in the present disclosure.

In addition, various different examples of the present disclosure can also be combined arbitrarily, as long as they do not violate the idea of the present disclosure, they should also be regarded as the content disclosed in the present disclosure.

What is claimed is:

1. A method of processing ray data for a Computed Tomography (CT) device, the method comprising:
   smoothing initial ray data based on collection of a detector of the CT device through at least two time windows to obtain smoothed ray data corresponding to each of the at least two time windows, wherein a window length of each of the at least two time windows is different, the initial ray data comprises attenuation values of rays passing through an object to be examined, and the initial ray data is obtained at a sampling frequency within a specified time period;

determining initial fluctuating data in the initial ray data based on the initial ray data and smoothed ray data corresponding to one of the at least two time windows, wherein the initial fluctuating data is associated with a fluctuation of the initial ray data due to occlusion of the rays by a collimator of the CT device that is configured to direct the rays towards the object to be examined; and removing the fluctuation from the initial ray data to obtain target ray data based on the smoothed ray data corresponding to each of the at least two time windows and the initial fluctuating data.

2. The method according to claim 1, wherein removing the fluctuation from the initial ray data to obtain the target ray data comprises:

determining one or more boundary intervals based on the smoothed ray data corresponding to each of the at least two time windows;

dividing the initial fluctuating data into first fluctuating data and second fluctuating data based on the one or more boundary intervals, wherein a peak-to-peak value of the first fluctuating data is less than a peak-to-peak value of the second fluctuating data;

replacing the second fluctuating data in the initial fluctuating data based on the first fluctuating data to obtain target fluctuating data; and obtaining the target ray data based on a difference between the initial ray data and the target fluctuating data.

3. The method according to claim 2, wherein determining the one or more boundary intervals based on the smoothed ray data corresponding to each of the at least two time windows comprises:

determining the one or more boundary intervals based on differences of the smoothed ray data corresponding to each pair of two time windows of the at least two time windows, wherein the one or more boundary intervals comprise one or more first fluctuating intervals and one or more second fluctuating intervals; and obtaining the first fluctuating data based on data in the one or more first fluctuating intervals of the initial fluctuating data and the second fluctuating data based on data in the one or more second fluctuating intervals of the initial fluctuating data.

4. The method according to claim 2, wherein replacing the second fluctuating data in the initial fluctuating data based on the first fluctuating data to obtain the target fluctuating data comprises:

converting the first fluctuating data into a fluctuating spectrum;

determining a fluctuating period corresponding to the fluctuation due to the occlusion of the rays by the collimator based on the fluctuating spectrum;

obtaining replacement data, whose duration is the fluctuating period, from the first fluctuating data; and replacing the second fluctuating data in the initial fluctuating data with the replacement data to obtain the target fluctuating data.

5. The method according to claim 4, wherein determining the fluctuating period corresponding to the fluctuation due to the occlusion of the rays by the collimator comprises:

determining a frequency point of a peak in the fluctuating spectrum; and determining the fluctuating period based on the frequency point of the peak, the sampling frequency, and the specified time period.

6. The method according to claim 1, wherein determining the initial fluctuating data in the initial ray data based on the initial ray data and the smoothed ray data corresponding to the one of the at least two time windows comprises:

determining the initial fluctuating data based on a difference between the initial ray data and the smoothed ray data corresponding to the one of the at least two time windows.

7. The method according to claim 6, wherein determining the initial fluctuating data in the initial ray data based on the initial ray data and the smoothed ray data corresponding to the one of the at least two time windows comprises:

obtaining the initial fluctuating data by filtering the difference with an attenuation threshold to remove data that exceeds the attenuation threshold in the difference.

8. The method according to claim 1, further comprising:

generating a CT image of the object based on the target ray data.

9. The method according to claim 1, wherein the rays are emitted from a ray emitter of the CT device, wherein the collection comprises second rays collected by the detector, the second rays being formed by the rays passing through the object to be examined, and wherein the attenuation values comprise differences between a first number of photons of the rays and a second number of photons of the second rays.

10. A device for processing ray data, the device comprising:

at least one processor, and at least one memory coupled to the at least one processor and storing programming instructions for execution by the at least one processor to:

smooth initial ray data based on collection of a detector of a CT device through at least two time windows to obtain smoothed ray data corresponding to each of the at least two time windows, wherein a window length of each of the at least two time windows is different, the initial ray data comprises attenuation values of rays passing through an object to be examined, and the initial ray data is obtained at a sampling frequency within a specified time period;

determine initial fluctuating data in the initial ray data based on the initial ray data and the smoothed ray data corresponding to one of the at least two time windows, wherein the initial fluctuating data is associated with a fluctuation of the initial ray data due to occlusion of the rays by a collimator of the CT device that is configured to direct the rays towards the object to be examined; and obtain target ray data by removing the fluctuation from the initial ray data based on the smoothed ray data corresponding to each of the at least two time windows and the initial fluctuating data.

11. The device according to claim 10, wherein the rays are emitted from a ray emitter of the CT device, wherein the collection comprises second rays collected by the detector, the second rays being formed by the rays passing through the object to be examined, and wherein the attenuation values comprise differences between a first number of photons of the rays and a second number of photons of the second rays.

12. The device according to claim 10, wherein the programming instructions are executable by the at least one processor to generate a CT image of the object based on the target ray data.

13. An electronic device comprising:
a ray emitter configured to emit first rays;
a collimator configured to direct the first rays toward an object to be examined; and
a detector configured to collect second rays that are formed by the first rays passing through the object to be examined;
at least one processor; and
at least one memory coupled to the at least one processor and storing programming instructions for execution by the at least one processor to:
smooth initial ray data obtained based on the second rays collected by the detector through at least two time windows to obtain smoothed ray data corresponding to each of the at least two time windows, wherein a window length of each of the at least two time windows is different, the initial ray data comprises attenuation values of the first rays passing through the object to be examined, and the initial ray data is obtained at a sampling frequency within a specified time period;
determine initial fluctuating data in the initial ray data based on the initial ray data and smoothed ray data corresponding to one of the at least two time windows, wherein the initial fluctuating data is associated with a fluctuation of the initial ray data due to occlusion of the first rays by the collimator; and
obtain target ray data by removing the fluctuation from the initial ray data based on the smoothed ray data corresponding to each of the at least two time windows and the initial fluctuating data.

14. The electronic device according to claim 13, wherein the programming instructions are executable by the at least one processor to:
determine one or more boundary intervals based on the smoothed ray data corresponding to each of the at least two time windows and divide the initial fluctuating data into first fluctuating data and second fluctuating data based on the one or more boundary intervals, wherein a peak-to-peak value of the first fluctuating data is less than a peak-to-peak value of the second fluctuating data;
replace the second fluctuating data in the initial fluctuating data based on the first fluctuating data to obtain target fluctuating data; and
obtain the target ray data based on a difference between the initial ray data and the target fluctuating data.

15. The electronic device according to claim 14, wherein the programming instructions are executable by the at least one processor to:
determine the one or more boundary intervals based on differences of the smoothed ray data corresponding to each pair of two time windows of the at least two time windows, wherein the one or more boundary intervals comprise one or more first fluctuating intervals and one or more second fluctuating intervals; and
obtain the first fluctuating data from the initial fluctuating data in the one or more first fluctuating intervals and the second fluctuating data from the initial fluctuating data in the one or more second fluctuating intervals.

16. The electronic device according to claim 14, wherein the programming instructions are executable by the at least one processor to:
convert the first fluctuating data into a first fluctuating spectrum;
determine a fluctuating period corresponding to the fluctuation due to the occlusion of the first rays by the collimator based on the fluctuating spectrum;
obtain replacement data, whose duration is the fluctuating period, from the first fluctuating data; and
replace the second fluctuating data in the initial fluctuating data with the replacement data to obtain the target fluctuating data.

17. The electronic device according to claim 16, wherein the programming instructions are executable by the at least one processor to:
determine a frequency point of a peak in the first fluctuating spectrum; and
determine the fluctuating period based on the frequency point of the peak, the sampling frequency, and the specified time period.

18. The electronic device according to claim 13, wherein the programming instructions are executable by the at least one processor to:
obtain the initial fluctuating data based on a difference between the initial ray data and the smoothed ray data corresponding to the one of the at least two time windows.

19. The electronic device according to claim 13, wherein the programming instructions are executable by the at least one processor to:
obtain a difference between the initial ray data and the smoothed ray data corresponding to the one of the at least two time windows; and
obtain the initial fluctuating data by filtering the difference with an attenuation threshold to remove data that exceeds the attenuation threshold.

20. The electronic device according to claim 13, wherein the programming instructions are executable by the at least one processor to:
generate a CT image of the object to be examined based on the target ray data.

* * * * *